US006838577B2

(12) United States Patent
Galley

(10) Patent No.: US 6,838,577 B2
(45) Date of Patent: Jan. 4, 2005

(54) PROCESSES FOR THE MANUFACTURE OF LACTONES

(75) Inventor: Richard A. Galley, Belle Mead, NJ (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 16 days.

(21) Appl. No.: 10/344,641
(22) PCT Filed: Apr. 17, 2001
(86) PCT No.: PCT/US01/12378
§ 371 (c)(1), (2), (4) Date: Jun. 13, 2003
(87) PCT Pub. No.: WO02/16346
PCT Pub. Date: Feb. 28, 2002

(65) Prior Publication Data
US 2004/0034238 A1 Feb. 19, 2004

Related U.S. Application Data
(60) Provisional application No. 60/227,537, filed on Aug. 24, 2000.
(51) Int. Cl.$^7$ .............................................. C07D 313/04
(52) U.S. Cl. ....................... 560/254; 525/438; 524/296; 549/272; 540/538
(58) Field of Search ........................ 560/254; 525/438; 524/296; 549/272; 540/538

(56) References Cited

U.S. PATENT DOCUMENTS

| 3,189,619 A | | 6/1965 | Aldridge et al. ............ 260/343 |
| 3,625,975 A | * | 12/1971 | Crampton et al. .......... 549/272 |
| 5,068,361 A | * | 11/1991 | Richter et al. .............. 549/273 |
| 5,817,883 A | | 10/1998 | Briggs et al. ............... 568/454 |
| 5,821,389 A | | 10/1998 | Briggs et al. ............... 568/454 |
| 5,981,769 A | | 11/1999 | Baur et al. .................. 549/266 |

FOREIGN PATENT DOCUMENTS

FR            1474903          2/1967

OTHER PUBLICATIONS

Grant R. Krow, "The Baeyer–Villiger Oxidation of Ketones and Aldehydes", *Organic Reactions*, vol. 13, Chapter 3, pp. 251–798 (1993).

* cited by examiner

*Primary Examiner*—James O. Wilson
*Assistant Examiner*—Devesh Khare

(57) ABSTRACT

Processes are disclosed for the manufacture of lactones, e.g., caprolactone, from hydoxy acids, e.g., 6-hydroxycaproic acid. The reaction is conducted over a suitable catalyst in the presence of water.

10 Claims, No Drawings

PROCESSES FOR THE MANUFACTURE OF LACTONES

This application claims the benefit of Provisional Application No. 60/227,537, filed Jun. 24, 2000.

FIELD OF THE INVENTION

The present invention relates to processes for the manufacture of lactones, e.g., caprolactone, from hydroxy acids, e.g., 6-hydroxycaproic acid.

BACKGROUND OF THE INVENTION

Caprolactone is a cyclic ester commonly used as a starting material in the preparation of oligomers and polymers.

One method of preparing caprolactone involves the Baeyer-Villiger oxidation cyclohexanone in the presence of a peracid such as peracetic acid. This method is described, for example, in Organic Reactions Volume 43, pages 251–798 (1993).

U.S. Pat. No. 3,189,619 discloses another method in which a 6-hydroxycaproic ester is reacted in a first stage with a trialkyl borate and the reaction product is then converted into caprolactone by heating at from 200° C. to 250° C. under reduced pressure. In another process, disclosed in French Patent 1,474,903, a 6-hydroxycaproic ester is heated to 150° to 350° C. in the presence of an oxide, such as magnesium oxide, zinc oxide, cadmium oxide, alumina or titanium dioxide, in the liquid phase under reduced pressure, and caprolactone is distilled off continuously.

U.S. Pat. No. 5,068,361 discloses a process for the preparation of caprolactone in which a 6-hydroxycaproic ester is heated at from 150° C. to 450° C. in the presence of an oxidic catalyst wherein 6-hydroxycaproic ester vapor is passed, together with an inert carrier gas, over a fixed-bed or fluidized-bed oxidic catalyst.

At col. 1, line 53 to 57, the patentees disclosed that:

6-Hydroxycaproic esters are advantageously vaporized at from 180° C. to 300° C. It has proven advantageous if solvents which are inert under the reaction conditions, such as esters, e.g., dioxane or tetrahydrofuran, are also vaporized simultaneously. Advantageously, from 50 to 90% strength by weight solutions of 6-hydroxycaproic esters in such solvents are used.

However, the use of organic solvents such as, for example, dioxane or tetrahydrofuran can pose health risks to humans and contaminate the environment. Thus, appropriate precautions must be taken to avoid such health risks and environmental contamination.

Furthermore, a by-product of the conversion of 6-hydroxycaproic esters to caprolactone by the above process is the corresponding alcohol. For example, each mole of 6-methoxycaproic acid converted to caprolactone, one mole of methanol is produced. The by-product alcohols are potentially harmful to the environment and must be recovered for disposal.

New processes for the manufacture of caprolactone, and other lactones, are desired which can limit or substantially eliminate the use of potentially harmful solvents and alcohol by-products.

SUMMARY OF THE INVENTION

In accordance with the present invention, processes are provided for the manufacture of lactones, e.g., caprolactone, from hydroxy acids having from about 4 to 10 carbon atoms per molecule, e.g., 6-hydroxycaproic acid. In the processes of the present invention, the hydroxy acid is reacted in the presence of water, e.g., water vapor, over a catalyst effective to remove water from said hydroxy acid and form the lactone. The amount of water used in the feedstream comprising the hydroxy acid is effective to enhance its conversion.

By virtue of the present invention, it is now possible to manufacture lactones without using organic solvents or producing undesirable by-products.

DETAILED DESCRIPTION OF THE INVENTION

The hydroxy acids suitable for use in accordance with the present invention those having from about 4 to 10 carbon atoms per molecule which are reactive. As used herein, the term "reactive hydroxy acids" means hydroxy acids which are capable of reacting, i.e., under the conditions of the process of the present invention, to form their corresponding lactones. Examples of such hydroxy acids include hydroxy acids such as 4-hydroxybutyric acid, 5-hydroxypentanoic acid, 5-hydroxy-2 methyl valeric acid, 5-hydroxy-4-methyl valeric acid, 6-hydroxycaproic acid, and 10-hydroxydecanoic acid. A preferred hydroxy acid is 6-hydroxycaproic acid.

The source of the hydroxy acids used in the present invention is not critical. For example, hydroxy acids can be obtained by oxidation of the corresponding hydroxy aldehyde. As an example, 6-hydroxy caproic acid can be obtained by oxidation of 6-hydroxyhexaldehyde, which in turn can be produced from butadiene as described in U.S. Pat. No. 5,817,883 and U.S. Pat. No. 5,821,389.

Another source of suitable 6-hydroxy caproic acid is by recovery from a waste stream produced during the production of cyclohexanone by oxidation of cyclohexane as described in U.S. Pat. No. 5,981,769.

Another source of 6-hydroxy caproic acid suitable for use in the process of this invention is a waste stream produced during the production of caprolactone such as, for example, by the Baeyer-Villiger reaction, or the reaction of cyclohexanone with a peracid.

Also, the feed used in the present invention can be low molecular weight oligomers of hydroxy acids. As an example, 6-hydroxy caproic acid dimers or trimers are suitable feeds.

In accordance with the present invention, a feedstream is provided which comprises one or more of the hydroxy acids and water. Advantageously, the amount of water is effective to enhance the selectivity of the hydroxy acid to the corresponding lactone. Preferably the selectivity is at least 50%, more preferably at least 70% and most preferably at least 80%. As used herein, the term "selectivity" means the moles of lactone produced per mole of hydroxy acid consumed in the reaction. Typically, the feedstream comprises from about 5 to 80 weight percent, preferably from about 10 to 50 weight percent of the hydroxy acid and from about 20 to 95% water, preferably from about 50 to 90% water. Preferably, the conversion is at least 50%, more preferably at least 80% and most preferably at least 90%. As used herein, the term "conversion" means the moles of hydroxy acid consumed per mole of hydroxy acid charged to the reaction. The feedstream may further comprise other materials, such as, for example, isomeric hydroxy acids, in amounts known to those skilled in the art.

In accordance with the present invention, the feedstream is passed to a reaction zone containing a catalyst effective to promote the conversion of the hydroxy acid to the corresponding lactone. The reaction zone may comprise any suitable apparatus for conducting the reaction, such as, for example, one or more fixed bed reactors or fluidized bed reactors.

Examples of suitable catalysts are oxides of elements of main groups 2 to 5 or subgroups 1 to 8 of the Periodic Table or oxides of rare earth metals or mixtures thereof. Examples are magnesium oxide, calcium oxide, zinc oxide, boron trioxide, titanium dioxide, silica, alumina, tin dioxide, bismuth oxide, copper oxide, lanthanum oxide, zirconium dioxide, vanadium oxides, chromium oxides, tungsten oxides, iron oxides, cerium oxides and neodynium oxides.

Silica, alumina or mixed silica-alumina catalysts are preferred. Alumina modified with a group I metal oxide, such as sodium oxide, or a group II metal oxide such as magnesium oxide or calcium oxide and mixed silica-alumina catalysts modified with a group I metal oxide and group II metal oxide are especially preferred. If a mixed silica-alumina catalyst is used, the preferred weight ratio of silica to alumina is from about three to one to about ten to one. More than one catalyst may be used. Suitable catalysts for use in the processes of the present invention are commercially available.

Optionally, a diluent such as, for example, an inert gas, e.g., nitrogen, may be used. When used, the diluent is typically present in an amount of from about 0.5 to 5.0 moles of diluent per mole of hydroxy acid.

Typically, the feedstream is passed in a vapor phase to the reaction zone at a space velocity of from about 100 to 1000 liters of vapor feed per liter of catalyst per hour.

Typically, the reaction is conducted at a temperature of from about 150 to 350° C., preferably from about 250 to 325° C., and at a pressure of from about 0.001 to 1.0 atmosphere ("atm"), preferably from about 0.01 to 0.7 atm.

Preferably, the reaction is conducted with a substantial absence of organic solvents, e.g., dioxane and tetrahydrofuran. As used herein, the term "substantial absence" means less than about 10 wt. %, preferably less than about 5 wt. % and more preferably less than about 1 wt. %, based on the total weight of the feedstream.

The processes of the present invention further comprise withdrawing from the reaction zone a product stream comprising a lactone and water.

The lactones produced by the processes of the present invention include those having from about 4 to 10 carbon atoms in the lactone ring. Preferred lactones include gamma-butyrolactone, delta-valerolactone, and epsilon-caprolactone. An especially preferred lactone is ε-caprolactone.

Typically the product stream will comprise from about 5 to 60 weight %, preferably from about 10 to 40 weight % of the lactone and from about 40 to 95 weight %, preferably from about 60 to 90 weight % water.

The reaction produces one mole of water for each mole of hydroxy acid reacted. Quite advantageously in accordance with the present invention, at least a portion of the water produced in the reaction may be recycled to comprise a portion of the feedstream. Any excess water can be removed from the process by conventional means. Indeed, after the initial start-up of the process, upon the achievements of stead state conditions, the process preferably does not require any water to be introduced to the process, since a sufficient quantity of water is generated by the reaction. Moreover, the amount of water recycled to the reactor can be adjusted to achieve the desired conversion.

The lactones produced by the process of the present invention have a variety of end uses. For example, caprolactone is typically used to make oligomers, polyols, homopolymers and copolymers, i.e., with other monomers such as diols, having a wide range of molecular weights, e.g., from about 1000 to 100,000 g/gmol (weight average).

The invention is further described with Examples which are provided for illustrative purposes and not intended to limit the scope of the claims which follow.

EXAMPLES

Comparative Example 1

(Thermal Reaction)

A 28 inch long stainless steel tube with internal diameter of 0.77 inches was charged with 215 cubic centimeters ("cc") of an inert, stainless steel sponge. The tube was heated to 300° C. and the pressure was reduced to 10 millimeters ("mm") Hg. A solution containing 10 wt % 6-hydroxycaporic acid in water was fed to the reactor at a rate of 65 grams per hour ("gph"). Nitrogen was also fed to the reactor at a rate of 40 cc per minute. The product was collected in a chilled receiver for 3.2 hours and then analyzed by gas chromotagraphy. Conversion of the 6-hydroxycaproic acid was 58% and the selectivity to caprolactone was 24%. The major by-products were oligomers of 6-hydroxycaproic acid.

Example 2

The reactor described in Example 1 was charged with 215 cc of a 4-10 mesh silica gel. The catalyst was heated to 300° C. and the pressure reduced to 10 mm Hg. A solution containing 10 wt % 6-hydroxycaproic acid in water was feed to the reactor at a rate of 49 gph for 4.2 hours. Nitrogen was also fed to the reactor at a rate of 40 cc/minute. The product was collected in a chilled receiver and analyzed by gas chromotagraphy. Conversion of the 6-hydroxycaproic acid was 94% and the selectivity to caprolactone was 59%. The major by-products were oligomers of 6-hydroxycaproic acid.

Example 3

The reactor described in Example 2 was charged with 76 cc of alumina. The catalyst was heated to 300° C. and the pressure reduced to 10 mm Hg. A solution containing 10 wt % 6-hydroxycaproic acid in water was fed to the reactor at a rate of 45 gph for 4.5 hours. Nitrogen was also fed to the reactor at a rate of 40 cc per minute. The product was collected in a chilled receiver and analyzed by gas chromatography. No 6-hydroxy caproic acid remained and the selectivity to caprolactone was 46%.

Example 4

Example 3 was repeated at 250° C. Product was collected for 5 hours and analyzed by gas chromatography. Conversion of 6-hydroxy caproic acid was 92% and the selectivity to caprolactone was 67%. The major by-products were oligomers of hydroxycaproic acid.

Example 5

The reactor described in Example 1 was charged with 76 cc of a commercially available diatomaceous earth catalyst containing 91% silica and 9% alumina. The catalyst was heated to 300° C. and the pressure reduced to 10 mm Hg. A solution containing 10% 6-hydroxy caproic acid in water was fed to the reactor at 22 gph for 2.4 hours. Nitrogen was also fed to the reactor at a rate of 40 cc per minute. The product was collected in a chilled receiver and analyzed by gas chromatography and size exclusion chromatography. The conversion of 6-hydroxy caproic acid was 78% and the selectivity to caprolactone was 96%.

Example 6

Example 5 was repeated at 325° C. The product was collected for 5 hours and analyzed by gas chromatography. Conversion of 6-hydroxy caproic acid was 88% and the selectivity to caprolactone was 76%. The major by-products were oligomers of hydroxycaproic acid.

Example 7

The reactor described in Example 1 was charged with 76 cc of a commercially available diatomaceous earth catalyst containing 72% silica, 8% alumina, and 20% calcium oxide. The catalyst was heated to 300° C. and the pressure reduced to 10 mm Hg. A solution containing 10% 6-hydroxy caproic acid in water was fed to the reactor at 23 gph for 4.5 hours. Nitrogen was also fed to the reactor at a rate of 40 cc per minute. The product was collected in a chilled receiver and analyzed by gas chromatography and size exclusion chromatography. The conversion of 6-hydroxy caproic acid was 92% and the selectivity to caprolactone was 92%.

Example 8

Example 7 was repeated at 325° C. The product was collected for 4.5 hours and analyzed by gas chromatography. Conversion of 6-hydroxy caproic acid was 97% and the selectivity to caprolactone was 94%. The major by-products were oligomers of hydroxycaproic acid.

Example 9

Example 8 was repeated with the 10% 6-hydroxy caproic acid in water feed rate increased to 46 gph. The product was collected for 4.5 hours and analyzed by gas chromatography. Conversion of 6-hydroxy caproic acid was 92% and the selectivity to caprolactone was 85%. The major by-products were oligomers of hydroxycaproic acid.

Example 10

Example 8 was repeated with the 10% 6-hydroxy caproic acid in water feed rate increased to 102 gph. The product was collected for 2 hours and analyzed by gas chromatography and size exclusion chromatography. Conversion of 6-hydroxy caproic acid was 85% and the selectivity to caprolactone was 86%. The major by-products were oligomers of hydroxycaproic acid.

Example 11

Example 8 was repeated with 50% 6-hydroxy caproic acid in water fed at a rate of 25 gph. The product was collected for 4.3 hours and analyzed by gas chromatography and size exclusion chromatography. Conversion of 6-hydroxy caproic acid was 88% and the selectivity to caprolactone was 94%.

Example 12

Example 8 was repeated at 325° C. and atmospheric pressure. The 10% hydroxy caproic acid in water feed rate was 55.5 gph. The product was collected for 3.8 hours and analyzed by gas chromatography and size exclusion chromatography. Conversion of 6-hydroxy caproic acid was 95% and the selectivity to caprolactone was 66%. The product was cloudy and contained oligomers of hydroxy caproic acid.

Example 13

The reactor described in Example 1 was charged with 76 cc of a commercially available catalyst containing 66% alumina, 30% magnesium oxide, and 4% graphite. The catalyst was heated to 325° C. and the pressure reduced to 10 mm Hg. A solution containing 10% 6-hydroxy caproic acid in water was fed to the reactor at 60 gph for 6.0 hours. Nitrogen was also fed to the reactor at a rate of 40 cc per minute. The product was collected in a chilled receiver and analyzed by gas chromatography and size exclusion chromatography. The conversion of 6-hydroxy caproic acid was 86% and the selectivity to caprolactone was 59%.

Example 14

The reactor described in Example 1 was charged with 76 cc of a gamma alumina catalyst containing 16% calcium oxide and 0.1% sodium oxide. The catalyst was heated to 325° C. at atmospheric pressure. A solution containing 10% 6-hydroxy caproic acid in water was fed to the reactor at about 60 gph for 2 hours. Nitrogen was also fed to the reactor at a rate of 40 cc per minute. The product was collected in a chilled receiver and analyzed by gas chromatography and size exclusion chromatography. The conversion of 6-hydroxy caproic acid was 100% and the selectivity to caprolactone was 43%. The pressure was then reduced to 250 mm Hg and the reaction continued for an additional 2 hours, after which time the conversion of 6-hydroxy caproic acid was 97% and the selectivity to caprolactone increased to 71%. The pressure was then reduced to 10 mm Hg and the reaction continued for another 6 hours, after which time the conversion of 6-hydroxy caproic acid was 96% and the selectivity to caprolactone increased to 95%

Example 15

The catalyst used in Example 14 was heated to 325° C. and the pressure in the reactor reduced to 10 mm Hg. A solution containing 10% 5-hydroxy valeric acid in water was fed to the reactor at about 45 gph for 3.3 hours. Nitrogen was also fed to the reactor at a rate of 40 cc per minute. The product was collected in a chilled receiver and analyzed by gas chromatography and size exclusion chromatography. The conversion of 5-hydroxy valeric acid was 100% and the selectivity to delta-valerolactone was 82%.

Example 16

Example 14 was repeated at 250° C. The product was collected in a chilled receiver and analyzed by gas chromatography and size exclusion chromatography. The conversion of 5-hydroxy valeric acid was 96% and the selectivity to delta-valerolactone was 69%.

What is claimed is:
1. A process for the manufacture of a lactone, comprising:
   (i) passing a feedstream comprising a reactive hydroxy acid having from about 4 to 10 carbon atoms per molecule in a vapor phase to a reaction zone containing a catalyst at conditions effective to convert the hydroxy acid to its corresponding lactone and water;
   (ii) withdrawing from the reaction zone a product stream comprising the lactone and water characterized in that the feedstream comprising an effective amount of water vapor to enhance the conversion.

2. The process of claim 1 wherein the feedstream comprises from about 20 to 90 weight percent water vapor based on the total weight of water vapor and hydroxy acid.

3. The process of claim 2 wherein the feedstream comprising from about 50 to 90 weight percent water vapor based on the total weight of water vapor and hydroxy acid.

4. The process of claim 1 wherein the catalyst is a heterogeneous oxide catalyst.

5. The process of claim 4 wherein the catalyst comprises silica, alumina, or mixtures thereof.

6. The process of claim 4 wherein the catalyst comprises a Group I metal oxide or a Group II metal oxide or mixtures thereof.

7. The process of claim 1 further comprising removing at least a portion of the water from the product stream and recycling the water to the reaction zone.

8. The process of claim 1 wherein the hydroxy acid is selected from the group consisting of 5-hydroxy valeric acid, 5 hydroxy 4-methyl valeric acid, 5-hydroxy 2-methyl valeric acid, and 6-hydroxycaproic acid and mixtures thereof.

9. The process of claim 1 wherein the lactone is selected from the group consisting of delta-valerolactone, delta-caprolactone, $\epsilon$-caprolactone, and mixtures thereof.

10. The process of claim 1 wherein the hydroxy acid is 6-hydroxycaproic acid and the lactone is $\epsilon$-caprolactone.

* * * * *